United States Patent [19]

Nylen et al.

[11] 4,311,789
[45] Jan. 19, 1982

[54] METHOD FOR SAMPLING AND MEASURING THE CONTENT OF A LOW-MOLECULAR WEIGHT COMPOUND IN A COMPLEX FLUID MEDIUM

[75] Inventors: Ulf T. G. Nylen; Lars A. G. Qvarnstrom, both of Lund, Sweden

[73] Assignee: Gambro AG, Sweden

[21] Appl. No.: 69,698

[22] Filed: Aug. 27, 1979

Related U.S. Application Data

[62] Division of Ser. No. 755,977, Dec. 30, 1976, Pat. No. 4,229,542.

[30] Foreign Application Priority Data

Dec. 31, 1975 [SE] Sweden ............................... 7600024

[51] Int. Cl.³ .................... C12Q 1/62; C12Q 1/58; C12Q 1/54
[52] U.S. Cl. .................................. 435/10; 435/12; 435/14; 435/18; 435/28; 23/230 B
[58] Field of Search .................. 210/22, 23, 321, 634, 210/635, 644, 645, 646, 647; 128/632, 630; 435/10, 12, 14, 18, 28, 287, 291; 422/50, 68, 81; 23/230 B; 424/2

[56] References Cited

U.S. PATENT DOCUMENTS

| | | | |
|---|---|---|---|
| 2,797,149 | 6/1957 | Skeggs | 435/12 |
| 2,893,324 | 9/1959 | Isreeli | 103/149 |
| 3,483,990 | 12/1969 | Litle et al. | 210/321 |
| 3,512,517 | 5/1970 | Kadish et al. | 128/2 |
| 3,721,623 | 3/1973 | Stana | 210/321 |
| 3,847,809 | 11/1974 | Kopf | 210/321 |
| 3,902,490 | 9/1975 | Jacobsen et al. | 210/321 |
| 3,919,051 | 11/1975 | Koch et al. | 435/14 |
| 3,993,560 | 11/1976 | Halpern | 435/240 |
| 4,123,353 | 10/1978 | Hakansson et al. | 210/22 |
| 4,229,542 | 10/1980 | Nylen et al. | 435/291 |

FOREIGN PATENT DOCUMENTS

| | | |
|---|---|---|
| 242177 | 10/1962 | Australia . |
| 162340 | of 0000 | New Zealand . |
| 219427 | 3/1968 | Sweden . |
| 816023 | 7/1959 | United Kingdom . |
| 160507 | 1/1964 | U.S.S.R. . |

OTHER PUBLICATIONS

Neff et al., "Measurement of Urea in Blood by Differential Heat of Hydrolysis", IBM Technical Disclosure Bulletin, vol. 11, No. 8, (1969), p. 898.
Bergmeyer et al., Methods of Enzymatic Analysis, vol. 4, Academic Press, N.Y., (1974), pp. 1890–1893.
Bergmeyer et al., Methods of Enzymatic Analysis, vol. 3, Academic Press, N.Y., (1974), pp. 1196–1205.

Primary Examiner—Thomas Wiseman
Attorney, Agent, or Firm—Lerner, David, Littenberg & Samuel

[57] ABSTRACT

A method is provided for sampling and measuring the content of a low-molecular weight compound, such as glucose, cholesterol, or urea, in a complex fluid medium to be sampled, such as blood. A dialyzer is placed in contact with the complex fluid medium so that it passes through the dialyzer. One or more semipermeable membranes are disposed within the complex fluid medium to form one or more passageways for the passage of dialysis fluid, with the passageways being substantially smaller in volume than the volume of the surrounding complex fluid medium. A fractional portion of the complex fluid medium is acted on by the dialysis fluid and dialyzed so that only a fractional portion of the low-molecular weight compound diffuses into the passageways containing the dialysis fluid to produce a dialysate in the passageways. The dialysate is then measured to determine the content of the low-molecular weight compound in the complex fluid medium.

22 Claims, 8 Drawing Figures

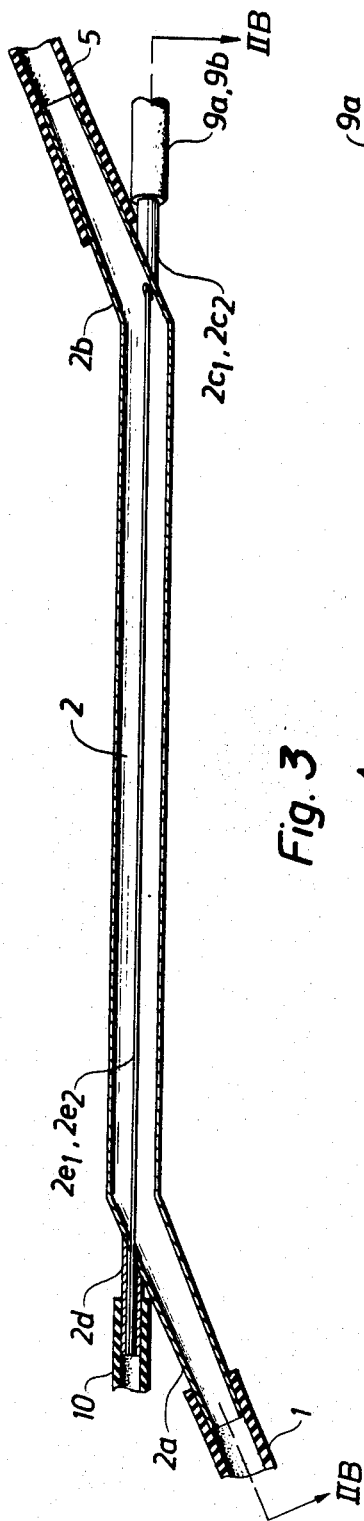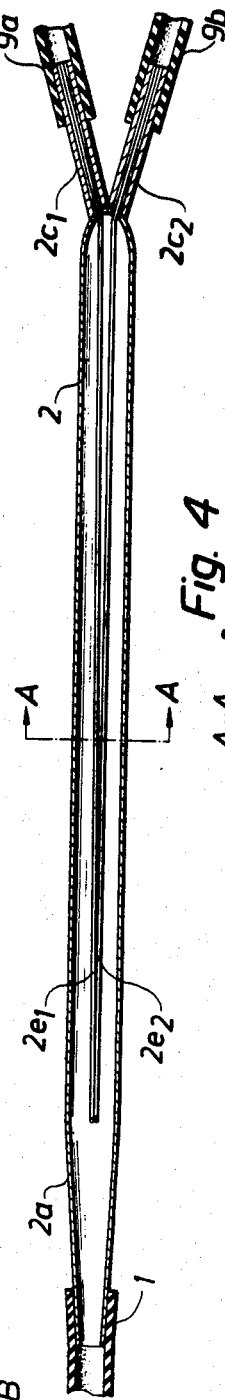

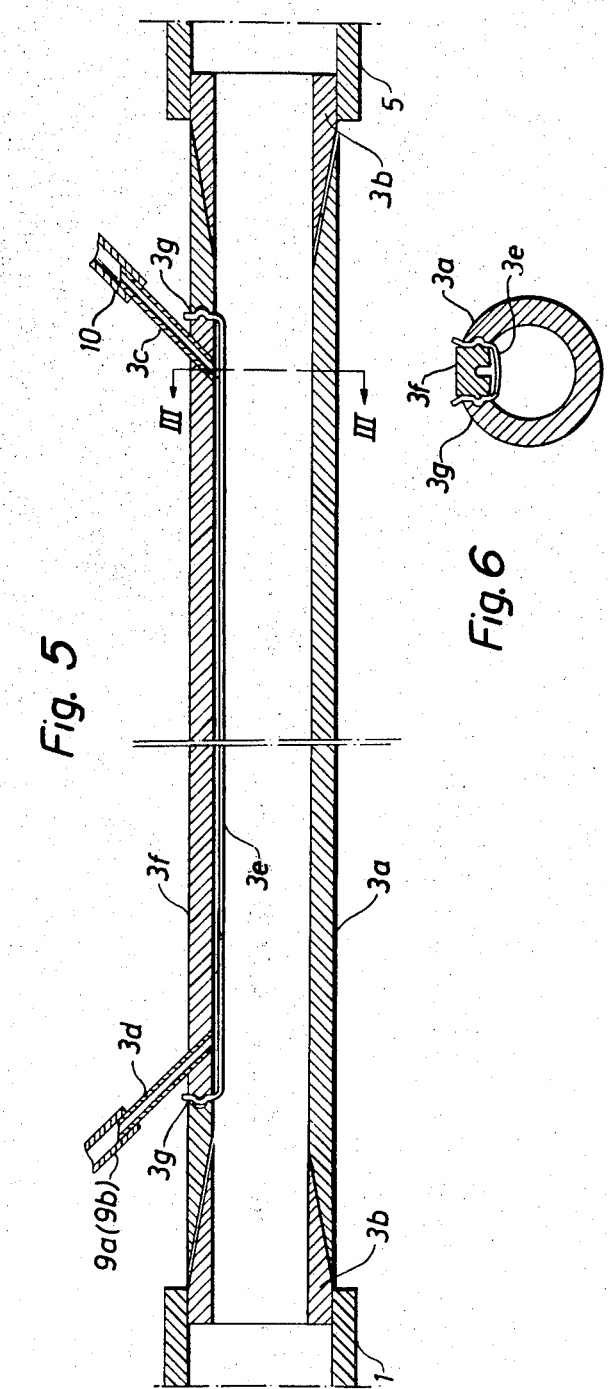

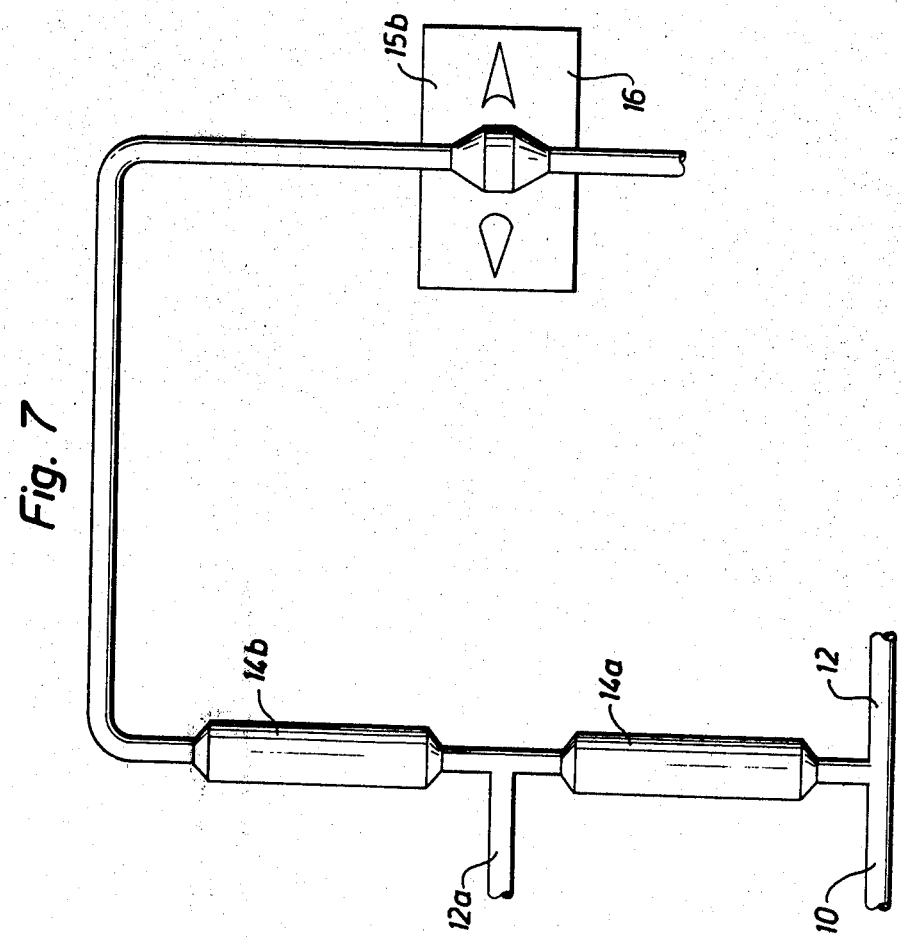

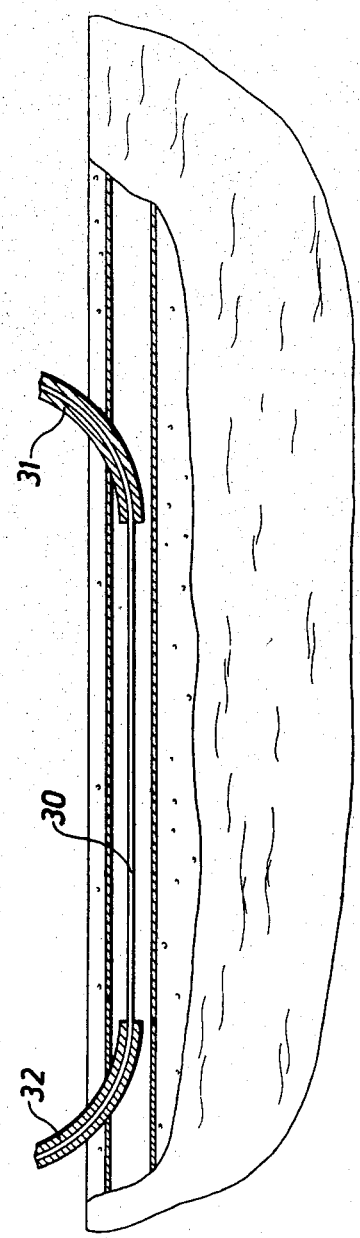

METHOD FOR SAMPLING AND MEASURING THE CONTENT OF A LOW-MOLECULAR WEIGHT COMPOUND IN A COMPLEX FLUID MEDIUM

This is a division of application Ser. No. 755,977, filed Dec. 30, 1976 U.S. Pat. No. 4,229,542.

FIELD OF THE INVENTION

The present invention relates to a method for the determination of the concentration of a low-molecular compound in a complex medium, e.g. blood, in particular in connection with medical treatment. The method in accordance with the present invention provides that a small portion of the complex medium is dialysed by a semipermeable membrane whereupon the measurement of the dialysate produced is carried out.

BACKGROUND OF THE INVENTION

It has long been desirable to provide a simple and efficient manner of measuring the content of a low-molecular compound, such as glucose or cholesterol, in a complex medium, such as blood. The present invention has provided such a method.

The determination of the concentration of the low-molecular compounds is carried out in connection with chemical reacting the dialysate with an enzyme, e.g. oxidation or hydrolysis, compound with formation of one or more readily analysable compounds. The measurement can be facilitated in some cases if the dialysate is diluted with a solution of reagent and/or a suitable buffer before the analysis is carried out.

The method in accordance with the invention in the preferred embodiment is intended to be applied to the measurement of glucose concentration n the blood of a patient, whereby the blood can be taken from a patient and introduced into a dialyzer and preferably be returned subsequently to the patient.

In such an application the dialyzer used is appropriately a "fibre-kidney" with preferably only one or a small number of fibres around which the blood is conducted whilst low-molecular compounds are transmitted to the dialysis fluid passing through, whereby the dialysate is formed which is to be measured. It is appropriate for the dialysis flow through each individual fibre to be controlled separately. As a result the flow through one fibre will be independent of the flow through another fibre. This is achieved appropriately in that each fibre is given a separate inlet and/or separate outlet and is connected to a separate pumping mechanism.

It will be clear to those versed in the art, that the method in accordance with the invention can of course also be applied to quantitative and/or qualitative determinations of low-molecular compounds in complex media other than blood, e.g. in micro-biological cultivating chambers.

In the method described above the low-molecular compounds diffuse over from the complex medium to the dialysis solution in the direction towards a higher pressure. If the dialysis is carried out during a short specified time, the result will be that only a very small part of the low-molecular compounds is removed from the complex medium. The concentration of the low-molecular compounds obtained in the dialysate will be much lower than in the complex medium. The concentration of the low-molecular compounds in the dialysate will, however, in practice be directly proportional to the concentration in the complex medium.

For the measurement of glucose in blood the dialysate is brought into contact with an enzyme, preferably glucose oxidase, appropriately immobilized on a solid matrix, e.g. porous glass. Glucose oxidase catalyzes the oxidation of glucose with consumption of oxygen, formation of hydrogen peroxide and liberation of propones. The difference in the concentration of $O_2$, $H^+$ or $H_2O_2$, which can be easily determined before and after the enzymatic reaction respectively by means of suitable electrodes or photometrically using e.g. a pH indicator, thus gives an answer which, owing to the proportionality, directly indicates the concentration of glucose in the complex medium.

The result of the measurement is appropriately calculator-processed directly so that the evaluated result can be used for treatment of the complex medium, e.g. blood, on which the measurement is carried out.

For the measurement of the glucose concentrations the enzyme hexokinase may also be used as an enzyme together with adenosine triphosphate (ATP), when glucose-6-phosphate and adenosine diphosphate (ADP) are formed with simultaneous changes, e.g. generation of heat, which can be measured. Similarly it is quite possible of course to allow the gluclose to participate in an electrochemical process, e.g. in a fuel cell with glucose and oxygen as reactants and obtain by this route a quantitative measure of the glucose concentration.

If the method in accordance with the invention is applied to the measurement of penicillin, penicillinase is suitable for use as the enzyme, the change in the pH which occurs being measured.

If the method in accordance with the invention is applied to the measurement of cholesterol, cholesterol oxidase is suitable for use as the enzyne, the change in the concentration of $O_2$ and/or $H_2O_2$ being measured.

If the method in accordance with the invention is applied to the measurement of uric acid, uricase is suitable for use as the enzyme, the change in the value of the pH being measured.

If the method in accordance with the invention is applied to the measurement of urea, urease is suitable for use as the enzyme and the $NH_3$ and/or $NH^{4+}$ formed or the rise in the value of the pH being measured.

If the method in accordance with the invention is applied to the measurement of any kind of substrate for any kind of enzyme, the determination can be carried out in most cases with the help of a thermistor, making use of the change in temperature which almost invariably takes place in enzymatic processes.

The measurment is carried out appropriately with maintaining constant pressure and temperature in the dialyzer, and, if the analyzing instrument is sensitive to the same, also at the place of actual measurement.

If a thin dialysis membrane with relatively small pores is chosen, the ultrafiltration of water will be small. Hence diffusion across the membrane will by and large be decisive. Consequently the dialysis purification is changed so insignificantly in the presence of substantial variations in pressure, that it is not necessary from a practical point of view to keep the pressure constant. It is desirable, however, that the pressure in the dialysis solution should be somewhat higher than in the surrounding complex medium, since the slight ultrafiltration which nevertheless will take place, will reduce the risk of "clotting" of high-molecular substances or cells on the fibre.

In the measurement of glucose concentrations it may be appropriate to dilute the dialysate with a weakly acid solution with the intention of lowering the pH to the pH optimum of the enzyme. If a photometric determination of the glucose concentration is desirable, another enzyme bed containing e.g. immobilized peroxidase may be used for a second enzymatic reaction between hydrogen peroxide and some substrate which gives rise to a colour reaction, e.g. ortho-toluidine. The substrate for this second enzyme stage may, depending upon circumstances, be added before or after the glucose oxidase bed.

The invention also relates to an arrangement for the realization of the above mentioned measurements in complex media. This arrangement is characterized by means for the realization of the dialysis of a small portion of the complex medium, these means comprising one or more lines for the introduction of the dialysis liquid and for the removal of the dialysate obtained, preferably via an enzyme transformation to a measuring unit.

The dialyzer appropriately consists of a fibre dialyzer with preferably one or two hollow semipermeable fibres with separate inlets through which the dialysis liquid is arranged to flow.

In certain cases it is desirable not be remove the complex medium e.g. blood, from its natural surroundings. As an alternative to the said fibre dialyzer, one or more semipermeable fibres provided with flexible tube connections may then be placed directly in the complex medium, e.g. in the blood stream, so as to bring about an intravascular dialysis.

If the membrane material and the flexible tubes are placed directly in the complex medium they should advantageously be treated in such a manner that minimum disturbance is caused in the complex material. When measuring in the blood stream it is appropriate, for example, to use heparinized material.

The arrangement in accordance with the invention appropriately comprises further means for the dilution of the dialysate with water, buffer and/or suitable reagent.

The analysis is made possible in certain cases by connecting in the arrangement in accordance with the invention between the dialyzer and a measuring unit an enzyme bed, e.g. a glass bed with immobilized enzyme for the transformation of the material that is to be measured to compounds which can be measured more readily. The desired enzymatic change can of course also be obtained in that the diluting solution after the dialyzer and/or the dialysis fluid contains the enzyme in free form.

In practice it has been found appropriate to combine the measuring unit with a computer for a direct utilization of the measuring result obtained so as to add the required components to the complex medium, e.g. blood, which is being examined.

In the following the invention will be described in detail with reference to the enclosed drawings which show by may of example preferred embodiments of the arrangement in accordance with the same.

FIG. 2, 3 and 4 show three views at right angles to one another of a fibre dialyzer which may form a detail in the arrangement according to FIG. 1.

FIG. 5 shows a plate dialyzer which may form a detail in the arrangement according to FIG. 1.

FIG. 6 shows a section along line III—III in FIG. 5.

FIG. 7 shows a set of two enzyme beds which may form a detail in FIG. 1.

FIG. 8 shows the dialysis process and the principle of intravascular dialysis.

Figure 1:
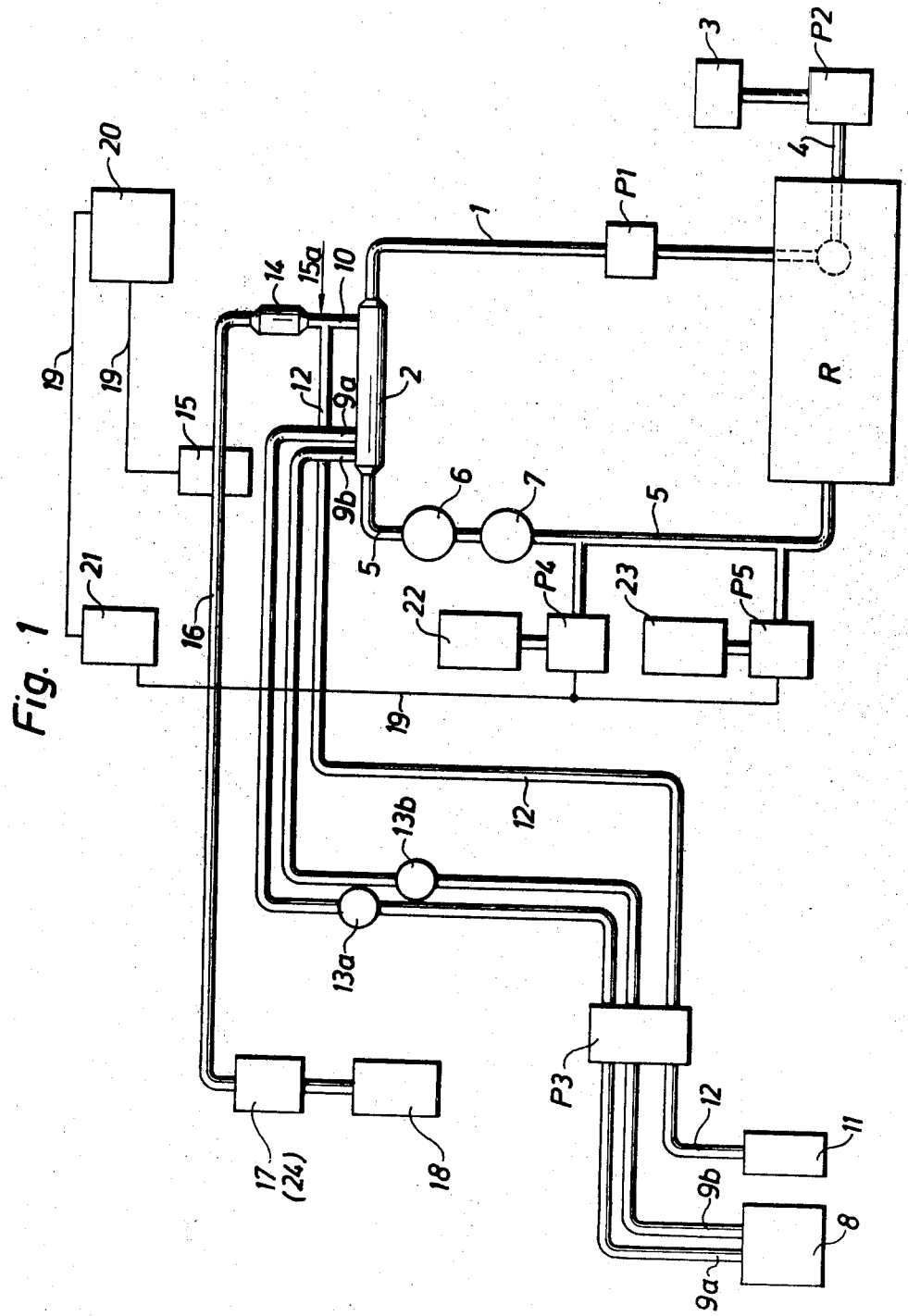
FIG. 1 shows a block diagram of the arrangement.

In FIG. 1 letter R refers to a reservoir for the complex medium which is to be analyzed. The medium is pumped with the help of a pump P1 via a line 1 to a dialyzer 2. If the medium consists for example of blood, the reservoir R may consist of a human vascular system. In this case it would be appropriate to pump by means of a pump P2 heparin from a reservoir 3 for this material via the lines 4 to a point near the inlet of line 1. In this case this is done so as to prevent coagulation of the blood. The medium under test is then conducted, as can be seen from FIG. 1, via a pressure gauge 6 and a pressure control 7 through a continuation of the line 5 back to the reservoir R.

The dialyzer may, for example, have the form which is shown on a larger scale in FIG. 2, 3, and 4, or in FIG. 5 and 6. In FIG. 2, 3 and 4 the dialyzer consists of a tube 2 to which the line 1 is connected via a tube nozzle $2a$. At the other end of the dialyzer the line 5 for the removal of the examined medium is connected by means of a tube nozzle $2b$. The dialyzer is provided in this case with three tube nozzles, $2c_1$, $2c_2$ and $2d$ which are arranged for the leading in and out respectively of two thin fibres $2e_1$ and $2e_2$ of a semipermeable membrane material, e.g. regenerated cellulose.

Dialysis fluid is conveyed by means of a multi-channel pump P3 from a reservoir 8 through lines $9a$ and $9b$ up to tube nozzles $2c_1$ and $2c_2$. Through these the dialysis fluid is introduced into the fibres $2e_1$ and $2e_2$ to be later discharged via the tube nozzle $2d$ into a line 10. Buffer solution and/or reagent solution is fed directly to this line 10 with the help of the same pump P3 via a line 12. The pressure gauges in the lines $9a$ and $9b$ are designated by $13a$ and $13b$. If differential measurement is required the diluted dialysate is then passed via a measuring point $15a$ and further through a unit 14 containing immobilized enzyme to a measuring point 15, e.g. a measuring electrode or a photometer, and further through a line 16 via a flowmeter 17 or a drop chamber 24 with drop counter for checking the rate of flow, and down to a drainage vessel 18. In FIG. 1 there is shown a general flowmeter 17 as well as a drop chamber 24. Naturally one of the two may be omitted.

The result obtained by means of e.g. measuring electrode or photocell 15 is passed via a line 19 and the measuring unit proper 20 to a computer 21. This computer may be arranged to control the pumps P4 and P5 for the pumping of a fluid from the reservoirs 22 and 23 directly to the line 5 for direct action upon the medium which is being examined. If it is e.g. a question of measurement of glucose in the blood of a patient the reservoir 22 may contain insulin and the reservoir 23 may contain glucose and/or glucagon.

In FIGS. 5 and 6, another embodiment of the dialyzer is shown and includes a tube $3a$ to which the line 1 is connected via a tube nozzle $3b$. The other end of the dialyzer is connected via another tube nozzle $3b$ to the line 5 for the removal of the examined medium. The dialyzer in this case is provided further with two more tube nozzles $3c$ and $3d$ which are arranged to introduce and to discharge, respectively, dialysis fluid under the semipermeable membrane which is designated $3e$.

For practical reaons the tube nozzles 3c and 3d have been shaped into a loose, coverlike part 3f which, with the help of a locking device 3g, is also used for clamping down the membrane 3e.

In FIG. 8 there is shown how the enzyme unit 4 can be made up of two enzyme beds arranged in series and connected to the line 10 from the dialyzer 2 and to the line 12 for diluting fluid etc. The numeral 12a indicates an alternative point of dilution between the two enzyme beds. This system may be used for bringing about and measuring a colour change and it is connected to a possible flowmeter and further to the drainage vessel 18 shown in FIG. 1.

In FIG. 9 finally is shown how the dialysis may be carried out directly in a blood vessel, in that a hollow fibre 30 of a semipermeable membrane material is led in and out via the leading tubes 31 and 32. Through these leading tubes the fibre is connected subsequently to lines corresponding to the lines 9a (or 9b) and 10 in FIG. 1, so that dialysis fluid can be made to pass through it in the same manner as through the fibres in dialyzer 2 in FIG. 1.

Naturally the invention is not confined solely to the embodiment described above, but may be varied within the framework of the following claims. For example, two or more of the above mentioned pumps may be co-ordinated in that, for example, one tube pump is made to act upon two or more flexible tubes.

The arrangement in accordance with the invention is particularly suitable in the medical treatment of a diabetic patient and can then serve as a so-called artificial pancreas. For those versed in the art it is clear, however, that the arrangement in accordance with the invention can also be used for the measurement and/or control of complex media other than blood.

We claim:

1. A method of sampling and measuring the content of a low molecular weight compound in a complex fluid medium to be sampled, comprising the steps of:
   providing a complex fluid medium to be sampled;
   arranging semi-permeable means in said complex fluid medium to be sampled so as to define one or more passageways in said complex fluid medium for the passage of dialysis fluid therethrough, said semi-permeable means being permeable to the low molecular weight compound in said complex fluid medium whose content is to be measured;
   conducting dialysis fluid through said passageways defined by said semi-permeable means in said complex fluid medium, said semi-permeable means being sized so that only a fractional portion of the volume of said complex fluid medium surrounding said semi-permeable means is dialyzed by said dialysis fluid being conducted through said passageways whereby a portion of the low molecular weight compound in said complex fluid medium diffuses into said passageways containing said dialysis fluid to thereby produce a dialysate in said passageways;
   maintaining the pressure of said dialysis fluid within said passageways higher than the pressure of said complex fluid medium to substantially reduce ultrafiltration from said complex fluid medium to said dialysis fluid; and
   measuring a property of said produced dialysate which is related to the content of the low molecular weight compound in said dialysate to determine the content of the low molecular weight compound in said complex fluid medium.

2. The method of claim 1 wherein said step of arranging semi-permeable means in said complex fluid medium comprises the step of placing one or more semi-permeable membranes directly in said complex fluid medium.

3. The method of claim 2 wherein the complex fluid medium is blood of a patient, and wherein the step of arranging one or more semi-permeable membranes comprises arranging one or more semi-permeable membranes in a blood vessel of the patient.

4. The method of claim 1 wherein the step of measuring comprises making a first measurement of a predetermined property of said dialysate; adding an enzyme to said dialysate to chemically react with said low-molecular weight compound in said dialysate to produce a change in said predetermined property of said dialysate which can be measured, and making a second measurement of said predetermined property in said changed, enzyme reacted dialysate.

5. The method of claim 4 wherein the step of measuring includes measuring the temperature change produced by said eyzymatic chemical reaction.

6. The method of claim 1 wherein the step of measuring is carried out while at least one of the pressure and the temperature in said dialyzer is kept constant.

7. The method of claim 5 wherein the step of measuring is carried out while at least one of the pressure and the temperature at the measuring point is kept constant.

8. The method of claim 1 wherein the step of measuring comprises chemically reacting said dialysate with an enzyme and then measuring a property of said enzyme reacted dialysate.

9. The method of claim 1 wherein said low-molecular weight compound is glucose, and said enzyme is glucose oxidase.

10. The method of claim 8 wherein said low-molecular weight compound is glucose, and said enzyme is hexokinase and adenosine triphosphate (ATP).

11. The method of claim 8 wherein said low-molecular weight compound is penicillin, and said enzyme is penicillinase.

12. The method of claim 8 wherein said low-molecular weight compound is cholesterol, and said enzyme is cholesterol oxidase.

13. The method of claim 8 wherein said low-molecular weight compound is urea, and said enzyme is urease.

14. The method of claim 8 wherein said low-molecular weight compound is uric acid, and said enzyme is uricase.

15. The method of claim 1 further including the step of returning said complex fluid medium, after dialysis, to the source of said complex fluid medium.

16. The method of claim 1 further including the step of diluting said dialysate with water, buffer, or reagent solution before measuring said dialysate.

17. The method of claim 1 further including the step of evaluating the results of said measuring step to treat said complex medium.

18. The method of claim 1 wherein the step of arranging semi-permeable means in said complex fluid medium to be sampled comprises arranging one or more semi-permeable membranes in said complex fluid medium to be sampled to form therein said one or more passageways for the passage of dialysis fluid therethrough.

19. The method of claim 18 further including the step of coating said semipermeable membrane with anticoagulant to prevent disturbances with the complex fluid medium.

20. The method of claim 18 wherein the volume of said passageways formed by said semi-permeable membranes is substantially smaller than the volume of said complex fluid medium surrounding said passageways.

21. The method of claim 20 wherein said dialyzer includes at least two semipermeable membranes, and said dialysis fluid is supplied to each of said membranes so that the flow through each is independent of the other.

22. The method of claim 1 wherein the step of arranging semi-permeable means in the complex fluid medium comprises providing a dialyzer having said semi-permeable means therein for forming said one or more passageways in said dialyzer for the passage of dialysis fluid therethrough, and connecting said dialyzer with said complex fluid medium to be sampled so that said complex fluid medium is conducted through said dialyzer along said semi-permeable means therein.

* * * * *

UNITED STATES PATENT AND TRADEMARK OFFICE
CERTIFICATE OF CORRECTION

PATENT NO. : 4,311,789
DATED : January 19, 1982
INVENTOR(S) : Nylen et al

It is certified that error appears in the above-identified patent and that said Letters Patent are hereby corrected as shown below:

On the title page the country of incorporation of the Assignee should read --Switzerland--.

Column 1, line 29, delete "compound".

Column 1, line 37, "n" should read --in--.

Column 5, line 5, "4" should read --14--.

Column 5, after line 11 and before line 12, insert --photometer 15b. The dialysate then passes via the line 16 to a--.

Signed and Sealed this

Twentieth Day of July 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,311,789
DATED : January 19, 1982
INVENTOR(S) : Nylen, et al.

It is certified that error appears in the above-identified patent and that said Letters Patent are hereby corrected as shown below:

On the title page, the Assignee should read --Gambro AB, Sweden--

Signed and Sealed this

Fifth Day of April 1983

[SEAL]

Attest:

GERALD J. MOSSINGHOFF

Attesting Officer     Commissioner of Patents and Trademarks